(12) United States Patent
Nakao et al.

(10) Patent No.: US 12,351,622 B2
(45) Date of Patent: Jul. 8, 2025

(54) MODIFIED PRODUCT OF Fc DOMAIN OF ANTIBODY

(71) Applicant: BiCA Therapeutics Inc., Kawasaki (JP)

(72) Inventors: Ryota Nakao, Kawasaki (JP); Yoshikatsu Izumi, Kawasaki (JP); Kunihiro Hattori, Kawasaki (JP)

(73) Assignee: BiCA Therapeutics Inc., Kawasaki (JP)

( * ) Notice: Subject to any disclaimer, the term of this patent is extended or adjusted under 35 U.S.C. 154(b) by 1056 days.

(21) Appl. No.: 17/311,085

(22) PCT Filed: Dec. 5, 2019

(86) PCT No.: PCT/JP2019/047620
§ 371 (c)(1),
(2) Date: Jun. 4, 2021

(87) PCT Pub. No.: WO2020/116560
PCT Pub. Date: Jun. 11, 2020

(65) Prior Publication Data
US 2022/0048981 A1    Feb. 17, 2022

(30) Foreign Application Priority Data

Dec. 5, 2018   (JP) .................................. 2018-228448

(51) Int. Cl.
*C07K 16/18* (2006.01)

(52) U.S. Cl.
CPC .......... *C07K 16/18* (2013.01); *C07K 2317/52* (2013.01); *C07K 2317/92* (2013.01); *C07K 2319/30* (2013.01)

(58) Field of Classification Search
CPC ................ C07K 16/18; C07K 2317/52; C07K 2317/92; C07K 2319/30
See application file for complete search history.

(56) References Cited

U.S. PATENT DOCUMENTS

| | | | |
|---|---|---|---|
| 7,083,784 B2 | 8/2006 | Dall'Acqua et al. |
| 7,670,600 B2 | 3/2010 | Dall'Acqua et al. |
| 7,704,497 B2 | 4/2010 | Dall'Acqua et al. |
| 8,012,476 B2 | 9/2011 | Dall'Acqua et al. |
| 8,323,962 B2 | 12/2012 | Dall'acqua et al. |
| 8,475,792 B2 | 7/2013 | Dall'Acqua et al. |
| 8,795,661 B2 | 8/2014 | Dall'Acqua et al. |
| 9,562,100 B2 | 2/2017 | Dall'Acqua et al. |
| 2003/0190311 A1 | 10/2003 | Dall'Acqua et al. |
| 2006/0198840 A1 | 9/2006 | Dall'Acqua et al. |
| 2007/0122403 A1 | 5/2007 | Dall'Acqua et al. |
| 2010/0189718 A1 | 7/2010 | Dall'Acqua et al. |
| 2011/0311454 A1 | 12/2011 | Dall'Acqua et al. |
| 2012/0093814 A1 | 4/2012 | Canada et al. |
| 2013/0052135 A1 | 2/2013 | Dall'Acqua et al. |
| 2013/0272964 A1 | 10/2013 | Dall'Acqua et al. |
| 2013/0281677 A1 | 10/2013 | Wilson et al. |
| 2014/0377181 A1 | 12/2014 | Dall'Acqua et al. |
| 2015/0056182 A1 | 2/2015 | Igawa et al. |
| 2017/0227547 A1 | 8/2017 | Emrich et al. |
| 2020/0181258 A1 | 6/2020 | Leger et al. |
| 2020/0216536 A1* | 7/2020 | Brondyk ................ C07K 16/18 |

FOREIGN PATENT DOCUMENTS

| | | |
|---|---|---|
| JP | 2012-521784 A | 9/2012 |
| JP | 2017-517745 A | 6/2017 |
| WO | 2002/60919 A2 | 8/2002 |
| WO | 2012/083370 A1 | 6/2012 |
| WO | 2013/081143 A1 | 6/2013 |
| WO | 2015/091910 A2 | 6/2015 |
| WO | 2018/009921 A1 | 1/2018 |
| WO | 2018/073185 A1 | 4/2018 |
| WO | 2020/082048 A1 | 4/2020 |

OTHER PUBLICATIONS

Nakao et al. U.S. Appl. No. 18/009,601. Fusion Protein Containing Erythropoietin Polypeptide. (Year: 2022).*
Dall'Acqua et al., Increasing the affinity of a human IgG1 for the neonatal Fc receptor: biological consequences, J. Immunol., 169(9):5171-80 (2002).
International Application No. PCT/JP2019/047620 International Preliminary Report on Patentability, mailed Jun. 17, 2021.
International Application No. PCT/JP2019/047620, International Search Report and Written Opinion, mailed Feb. 10, 2020.
Mannan et al., Monoclonal Antibody Clearance Impact of Modulating the Interaction of IGG with The Neonatal Fc Receptor, J. Bio. Chem., 282(3):1709-1717 (2007).
Strietzel et al., In vitro functional characterization of feline IgGs, Vet. Immunol. Immunopathol., 158(3-4):214-23 (2014).
Yeung et al., Engineering Human IgG1 Affinity to Human Neonatal Fc Receptor: Impact of Affinity Improvement on Pharmacokinetics in Primates, J. Immunol., 182(12):7663-71 (2009).

* cited by examiner

*Primary Examiner* — Brad Duffy
*Assistant Examiner* — Elizabeth A Shupe
(74) *Attorney, Agent, or Firm* — MARSHALL, GERSTEIN & BORUN LLP

(57) ABSTRACT

The present invention is directed to a variant of a parent polypeptide containing an Fc region of a dog or cat IgG, that shows a higher binding activity to a dog or cat neonatal Fc receptor (FcRn) than a binding activity of the parent polypeptide to a dog or cat FcRn, wherein the Fc region contains at least one amino acid modification. The variant shows an enhanced FcRn binding activity under acidic conditions. Using the variant, therefore, an antibody (IgG) and Fc fusion protein having longer retention in plasma can be provided.

2 Claims, No Drawings
Specification includes a Sequence Listing.

```
SEQUENCE LISTING

<160> NUMBER OF SEQ ID NOS: 11

<210> SEQ ID NO 1
<211> LENGTH: 219
<212> TYPE: PRT
<213> ORGANISM: Canis familiaris

<400> SEQUENCE: 1

Ala Pro Glu Met Leu Gly Gly Pro Ser Val Phe Ile Phe Pro Pro Lys
1               5                   10                  15

Pro Lys Asp Thr Leu Leu Ile Ala Arg Thr Pro Glu Val Thr Cys Val
            20                  25                  30

Val Val Asp Leu Asp Pro Glu Asp Pro Glu Val Gln Ile Ser Trp Phe
        35                  40                  45

Val Asp Gly Lys Gln Met Gln Thr Ala Lys Thr Gln Pro Arg Glu Glu
    50                  55                  60

Gln Phe Asn Gly Thr Tyr Arg Val Val Ser Val Leu Pro Ile Gly His
65                  70                  75                  80

Gln Asp Trp Leu Lys Gly Lys Gln Phe Thr Cys Lys Val Asn Asn Lys
                85                  90                  95

Ala Leu Pro Ser Pro Ile Glu Arg Thr Ile Ser Lys Ala Arg Gly Gln
            100                 105                 110

Ala His Gln Pro Ser Val Tyr Val Leu Pro Pro Ser Arg Glu Glu Leu
        115                 120                 125

Ser Lys Asn Thr Val Ser Leu Thr Cys Leu Ile Lys Asp Phe Phe Pro
    130                 135                 140

Pro Asp Ile Asp Val Glu Trp Gln Ser Asn Gly Gln Gln Glu Pro Glu
145                 150                 155                 160
```

```
Ser Lys Tyr Arg Thr Thr Pro Pro Gln Leu Asp Glu Asp Gly Ser Tyr
            165                 170                 175

Phe Leu Tyr Ser Lys Leu Ser Val Asp Lys Ser Arg Trp Gln Arg Gly
            180                 185                 190

Asp Thr Phe Ile Cys Ala Val Met His Glu Ala Leu His Asn His Tyr
            195                 200                 205

Thr Gln Glu Ser Leu Ser His Ser Pro Gly Lys
            210                 215

<210> SEQ ID NO 2
<211> LENGTH: 219
<212> TYPE: PRT
<213> ORGANISM: Felis catus

<400> SEQUENCE: 2

Pro Pro Glu Met Leu Gly Gly Pro Ser Ile Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asp Val Gln Ile Thr Trp Phe
        35                  40                  45

Val Asp Asn Thr Gln Val Tyr Thr Ala Lys Thr Ser Pro Arg Glu Glu
50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Pro Ile Glu Arg Thr Ile Ser Lys Ala Lys Gly Gln
            100                 105                 110

Pro His Glu Pro Gln Val Tyr Val Leu Pro Pro Ala Gln Glu Glu Leu
        115                 120                 125

Ser Arg Asn Lys Val Ser Val Thr Cys Leu Ile Lys Ser Phe His Pro
130                 135                 140

Pro Asp Ile Ala Val Glu Trp Glu Ile Thr Gly Gln Pro Glu Pro Glu
145                 150                 155                 160

Asn Asn Tyr Arg Thr Thr Pro Pro Gln Leu Asp Ser Asp Gly Thr Tyr
            165                 170                 175

Phe Val Tyr Ser Lys Leu Ser Val Asp Arg Ser His Trp Gln Arg Gly
            180                 185                 190

Asn Thr Tyr Thr Cys Ser Val Ser His Glu Ala Leu His Ser His His
            195                 200                 205

Thr Gln Lys Ser Leu Thr Gln Ser Pro Gly Lys
            210                 215

<210> SEQ ID NO 3
<211> LENGTH: 234
<212> TYPE: PRT
<213> ORGANISM: Homo sapiens

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45
```

Val Ala Ser Ile Thr Tyr Asp Gly Ser Thr Asn Tyr Asn Pro Ser Val
50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro
225                 230

<210> SEQ ID NO 4
<211> LENGTH: 218
<212> TYPE: PRT
<213> ORGANISM: Homo sapiens

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 5
<211> LENGTH: 19
<212> TYPE: PRT
<213> ORGANISM: Artificial Sequence
<220> FEATURE:
<223> OTHER INFORMATION: secretion signal peptide

<400> SEQUENCE: 5

Met Glu Phe Gly Leu Ser Trp Val Phe Leu Val Ala Leu Phe Arg Gly
1               5                   10                  15

Val Gln Cys

<210> SEQ ID NO 6
<211> LENGTH: 22
<212> TYPE: PRT
<213> ORGANISM: Artificial Sequence
<220> FEATURE:
<223> OTHER INFORMATION: secretion signal peptide

<400> SEQUENCE: 6

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 7
<211> LENGTH: 297
<212> TYPE: PRT
<213> ORGANISM: Canis familiaris

<400> SEQUENCE: 7

Met Gly Val Pro Arg Pro Arg Ser Trp Gly Leu Gly Phe Leu Leu Phe
1               5                   10                  15

Leu Leu Pro Thr Leu Arg Ala Ala Asp Ser His Leu Ser Leu Leu Tyr
            20                  25                  30

His Leu Thr Ala Val Ser Ala Pro Pro Gly Thr Pro Ala Phe Trp
        35                  40                  45

Ala Ser Gly Trp Leu Gly Pro Gln Gln Tyr Leu Ser Tyr Asn Asn Leu
    50                  55                  60

Arg Ala Gln Ala Glu Pro Tyr Gly Ala Trp Val Trp Glu Asn Gln Val
65                  70                  75                  80

Ser Trp Tyr Trp Glu Lys Glu Thr Thr Asp Leu Arg Thr Lys Glu Gly
                85                  90                  95

Leu Phe Leu Glu Ala Leu Lys Ala Leu Gly Asp Gly Pro Tyr Thr
                100                 105                 110

Leu Gln Gly Leu Leu Gly Cys Glu Leu Gly Pro Asp Asn Thr Ser Val
            115                 120                 125

Pro Val Ala Lys Phe Ala Leu Asn Gly Glu Asp Phe Met Thr Phe Asp
        130                 135                 140

Pro Lys Leu Gly Thr Trp Asn Gly Asp Trp Pro Glu Thr Glu Thr Val
145                 150                 155                 160

Ser Lys Arg Trp Met Gln Gln Ala Gly Ala Val Ser Lys Glu Arg Thr
                165                 170                 175
```

```
Phe Leu Leu Tyr Ser Cys Pro Gln Arg Leu Leu Gly His Leu Glu Arg
            180                 185                 190

Gly Arg Gly Asn Leu Glu Trp Lys Glu Pro Pro Ser Met Arg Leu Lys
        195                 200                 205

Ala Arg Pro Gly Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Ser Gly Glu Gly Asp Phe Gly Pro Asn Gly Asp Gly Ser
                245                 250                 255

Phe His Ala Trp Ser Ser Leu Thr Val Lys Ser Gly Asp Glu His His
            260                 265                 270

Tyr Arg Cys Leu Val Gln His Ala Gly Leu Pro Gln Pro Leu Thr Val
        275                 280                 285

Glu Leu Glu Ser Pro Ala Lys Ser Ser
    290                 295

<210> SEQ ID NO 8
<211> LENGTH: 297
<212> TYPE: PRT
<213> ORGANISM: Felis catus

<400> SEQUENCE: 8

Met Gly Val Pro Arg Pro Gln Pro Trp Gly Leu Gly Phe Leu Leu Phe
1               5                   10                  15

Leu Leu Pro Thr Leu Arg Ala Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Asn Leu
    50                  55                  60

Arg Ala Gln Ala Glu Pro Cys Gly Ala Trp Val Trp Glu Asn Gln Val
65                  70                  75                  80

Ser Trp Tyr Trp Glu Lys Glu Thr Thr Asp Leu Arg Asn Lys Gln Glu
                85                  90                  95

Leu Phe Leu Glu Ala Leu Lys Val Leu Gly Glu Gly Gly Pro Tyr Thr
            100                 105                 110

Leu Gln Gly Leu Leu Gly Cys Glu Leu Gly Pro Asp Asn Ala Ser Val
        115                 120                 125

Pro Val Ala Lys Phe Ala Leu Asn Gly Glu Asp Phe Met Asp Phe Asp
    130                 135                 140

Pro Lys Leu Gly Thr Trp Ser Gly Glu Trp Pro Glu Thr Glu Thr Ile
145                 150                 155                 160

Ser Lys Arg Trp Met Gln Glu Ala Gly Ala Val Ser Lys Glu Arg Thr
                165                 170                 175

Phe Leu Leu Asn Ser Cys Pro Gln Arg Leu Leu Gly His Leu Glu Arg
            180                 185                 190

Gly Arg Gly Asn Leu Glu Trp Lys Glu Pro Pro Ser Met Arg Leu Lys
        195                 200                 205

Ala Arg Pro Gly Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Ser Gly Glu Gly Asp Phe Gly Pro Asn Gly Asp Gly Ser
                245                 250                 255
```

```
Phe His Ala Trp Ser Ser Leu Thr Val Lys Ser Gly Asp Glu His His
                260                 265                 270

Tyr Arg Cys Leu Val Gln His Ala Gly Leu Pro Gln Pro Leu Thr Val
            275                 280                 285

Glu Leu Glu Ser Pro Ala Lys Ser Ser
        290                 295

<210> SEQ ID NO 9
<211> LENGTH: 8
<212> TYPE: PRT
<213> ORGANISM: Artificial Sequence
<220> FEATURE:
<223> OTHER INFORMATION: His tag

<400> SEQUENCE: 9

His His His His His His His His
1               5

<210> SEQ ID NO 10
<211> LENGTH: 125
<212> TYPE: PRT
<213> ORGANISM: Canis familiaris

<400> SEQUENCE: 10

Met Ala Pro Arg Pro Ala Leu Ala Thr Ala Gly Phe Leu Ala Leu Leu
1               5                   10                  15

Leu Ile Leu Leu Ala Ala Cys Arg Leu Asp Ala Val Gln His Pro Pro
            20                  25                  30

Lys Ile Gln Val Tyr Ser Arg His Pro Ala Glu Asn Gly Lys Pro Asn
        35                  40                  45

Phe Leu Asn Cys Tyr Val Ser Gly Phe His Pro Pro Glu Ile Glu Ile
    50                  55                  60

Asp Leu Leu Lys Asn Gly Lys Glu Met Lys Ala Glu Gln Thr Asp Leu
65                  70                  75                  80

Ser Phe Ser Lys Asp Trp Thr Phe Tyr Leu Leu Val His Thr Glu Phe
                85                  90                  95

Thr Pro Asn Glu Gln Asp Glu Phe Ser Cys Arg Val Lys His Val Thr
            100                 105                 110

Leu Ser Glu Pro Gln Ile Val Lys Trp Asp Arg Asp Asn
        115                 120                 125

<210> SEQ ID NO 11
<211> LENGTH: 118
<212> TYPE: PRT
<213> ORGANISM: Felis catus

<400> SEQUENCE: 11

Met Ala Arg Phe Val Val Leu Val Leu Leu Gly Leu Leu Tyr Leu Ser
1               5                   10                  15

His Leu Asp Ala Val Gln His Ser Pro Lys Val Gln Val Tyr Ser Arg
            20                  25                  30

His Pro Ala Glu Asn Gly Lys Pro Asn Phe Leu Asn Cys Tyr Val Ser
        35                  40                  45

Gly Phe His Pro Pro Gln Ile Asp Ile Thr Leu Met Lys Asn Gly Lys
    50                  55                  60

Lys Met Glu Ala Glu Gln Thr Asp Leu Ser Phe Asn Arg Asp Trp Thr
65                  70                  75                  80

Phe Tyr Leu Leu Val His Thr Glu Phe Thr Pro Thr Val Glu Asp Glu
```

-continued

```
                85                  90                  95
Tyr Ser Cys Gln Val Asn His Thr Thr Leu Ser Glu Pro Lys Val Val
            100                 105                 110

Lys Trp Asp Arg Asp Met
            115
```

MODIFIED PRODUCT OF Fc DOMAIN OF ANTIBODY

CROSS REFERENCE TO RELATED APPLICATIONS

This application is a U.S. National Stage of International Application No. PCT/JP2019/047620, filed Dec. 5, 2019, which claims the benefit of Japanese Patent Application No. 2018-228448, filed Dec. 5, 2018, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "56870_Seqlisting.txt." The Sequence Listing was created on Jun. 2, 2021, and is 16,325 Bytes in size. The subject matter of the Sequence Listing is incorporated by reference herein in its entirety.

TECHNICAL FIELD

The present invention relates to Fc region variants of dog or cat IgG, particularly, Fc region variants in which binding affinity with neonatal Fc receptor is enhanced.

BACKGROUND ART

Neonatal Fc receptor (hereinafter to be also referred to as FcRn) avoids lysosomal degradation of IgG by binding to the Fc region of IgG and recycling same into plasma. IgG shows prolonged retention in plasma by binding to FcRn. Binding of IgG to FcRn is observed only under acidic conditions (e.g., pH 6.0), and the binding is scarcely observed under neutral conditions (e.g., pH 7.4). Generally, IgG is non-specifically incorporated into cells via endocytosis. It returns to the cell surface by binding to FcRn in endosome under acidic conditions in the endosome and is recycled by dissociating from FcRn under neutral conditions in plasma, resulting in longer retention in plasma than other plasma proteins. IgG that did not bind to FcRn in endosome proceeds to lysosome where it is degraded.

As a method for improving retention of IgG in plasma, a method for improving the binding ability to FcRn under acidic conditions in human has been reported. By increasing the binding ability to FcRn under acidic conditions by introducing amino acid substitution into the Fc region of IgG, the recycling efficiency from endosome to plasma increases, thus resulting in improved retention in plasma (patent documents 1, 2, non-patent documents 1-3).

In addition, cytokines or soluble membrane receptors, which is fused with Fc region of IgG, and the like (Fc fusion proteins) have been developed as therapeutic pharmaceutical products for human. These achieve long retention in plasma through binding to FcRn, like IgG.

As described above, biopharmaceutical products have been developed for humans by modifying and applying the binding between the Fc region of IgG and FcRn, and the development of biopharmaceutical products with similarly-improved retention in plasma has been desired for animals other than human, such as dog, cat, and the like.

However, modification of amino acids in the Fc region that improves and advances retention of antibodies in plasma in dogs and cats is not known.

Document List

Patent Documents patent document 1: WO 2002/060919
patent document 2: WO 2012/083370

Non-Patent Documents non-patent document 1: Yeung Y A, et al., J. Immunol. (2009) 182, 7663-71.
non-patent document 2: Datta-Mannan A, et al., J. Biol. Chem. (2007) 282, 1709-17.
non-patent document 3: Dall'Acqua W F, et al., J. Immunol. (2002) 169, 5171-80.

SUMMARY OF INVENTION

Technical Problem

The present invention aims to provide a variant of the Fc region of dog and cat IgG, which shows enhanced binding ability to FcRn under acidic conditions, particularly, improved retention in plasma.

Solution to Problem

In an attempt to solve the aforementioned problems, the present inventors have conducted intensive studies of amino acid modifications in the Fc region of IgG that can significantly potentiate the binding with FcRn under pH acidic range conditions as compared to the Fc region of natural IgG, and found amino acid modifications capable of enhancing the FnRn binding activity as compared to the wild type (hereinafter to be also referred to as the amino acid modification of the present invention), which resulted in the completion of the present invention.

Accordingly, the present invention provides the following.

[1] A variant of a parent polypeptide comprising an Fc region of a dog or cat IgG, that shows a higher binding activity to a dog or cat neonatal Fc receptor (FcRn) than a binding activity of the parent polypeptide to a dog or cat FcRn under acidic conditions, wherein the Fc region comprises at least one amino acid modification.
[2] The variant of the above-mentioned [1], wherein the parent polypeptide constitutes an antibody.
[3] The variant of the above-mentioned [1] or [2], wherein the parent polypeptide comprises an Fc region of dog IgG.
[4] The variant of the above-mentioned [1] or [2], wherein the parent polypeptide comprises an Fc region of cat IgG.
[5] The variant of the above-mentioned [3], wherein the amino acid modification in the Fc region comprises at least one selected from the group consisting of
(i) substitution of the 252-position leucine with tyrosine or threonine,
(ii) substitution of the 254-position alanine with threonine,
(iii) substitution of the 256-position threonine with glutamic acid,
(iv) substitution of the 308-position isoleucine with proline,
(v) substitution of the 428-position methionine with leucine,
(vi) substitution of the 433-position histidine with leucine, (vii) substitution of the 434-position asparagine with alanine, serine, tyrosine or phenylalanine,
(viii) substitution of the 436-position tyrosine with threonine,
(ix) substitution of the 438-position glutamine with arginine, and
(x) substitution of the 440-position serine with glutamic acid (wherein the numbering of amino acids in the Fc region is based on EU Index of Kabat using Fc region of human antibody as the standard).
[6] The variant of the above-mentioned [5], wherein the amino acid modifications in the Fc region are
(i) substitution of the 434-position asparagine with alanine,
(ii) substitution of the 436-position tyrosine with threonine,
(iii) substitution of the 438-position glutamine with arginine, and
(iv) substitution of the 440-position serine with glutamic acid.
[7] The variant of the above-mentioned [5], wherein the amino acid modifications in the Fc region are
(i) substitution of the 428-position methionine with leucine,
(ii) substitution of the 434-position asparagine with alanine,
(iii) substitution of the 436-position tyrosine with threonine,
(iv) substitution of the 438-position glutamine with arginine, and
(v) substitution of the 440-position serine with glutamic acid.
[8] The variant of the above-mentioned [5], wherein the amino acid modifications in the Fc region are
(i) substitution of the 428-position methionine with leucine,
(ii) substitution of the 434-position asparagine with alanine,
(iii) substitution of the 438-position glutamine with arginine, and
(iv) substitution of the 440-position serine with glutamic acid.
[9] The variant of the above-mentioned [5], wherein the amino acid modifications in the Fc region are
(i) substitution of the 252-position leucine with tyrosine,
(ii) substitution of the 254-position alanine with threonine, and
(iii) substitution of the 256-position threonine with glutamic acid.
[10] The variant of the above-mentioned [5], wherein the amino acid modifications in the Fc region are
(i) substitution of the 428-position methionine with leucine, and
(ii) substitution of the 434-position asparagine with serine.
[11] The variant of the above-mentioned [5], wherein the amino acid modifications in the Fc region are
(i) substitution of the 308-position isoleucine with proline, and
(ii) substitution of the 434-position asparagine with tyrosine.
[12] The variant of the above-mentioned [5], wherein the amino acid modifications in the Fc region are
(i) substitution of the 252-position leucine with threonine,
(ii) substitution of the 254-position alanine with threonine,
(iii) substitution of the 256-position threonine with glutamic acid,
(iv) substitution of the 433-position histidine with leucine, and
(v) substitution of the 434-position asparagine with phenylalanine.
[13] The variant of the above-mentioned [4], wherein the amino acid modification in the Fc region includes at least one selected from the group consisting of
(i) substitution of the 252-position serine with tyrosine or threonine,
(ii) substitution of the 254-position serine with threonine,
(iii) substitution of the 256-position threonine with glutamic acid,
(iv) substitution of the 259-position valine with isoleucine,
(v) substitution of the 308-position isoleucine with proline or phenylalanine,
(vi) substitution of the 428-position serine with leucine,
(vii) substitution of the 433-position histidine with leucine,
(viii) substitution of the 434-position serine with alanine, tyrosine or phenylalanine,
(ix) substitution of the 436-position histidine with threonine,
(x) substitution of the 438-position glutamine with arginine, and
(xi) substitution of the 440-position serine with glutamic acid (wherein the numbering of amino acids in the Fc region is based on EU Index of Kabat using Fc region of human antibody as the standard).
[14] The variant of the above-mentioned [13], wherein the amino acid modifications in the Fc region are
(i) substitution of the 434-position serine with alanine,
(ii) substitution of the 436-position histidine with threonine,
(iii) substitution of the 438-position glutamine with arginine, and
(iv) substitution of the 440-position serine with glutamic acid.
[15] The variant of the above-mentioned [13], wherein the amino acid modifications in the Fc region are
(i) substitution of the 428-position serine with leucine,
(ii) substitution of the 434-position serine with alanine,
(iii) substitution of the 436-position histidine with threonine,
(iv) substitution of the 438-position glutamine with arginine, and
(v) substitution of the 440-position serine with glutamic acid.
[16] The variant of the above-mentioned [13], wherein the amino acid modifications in the Fc region are
(i) substitution of the 428-position serine with leucine,
(ii) substitution of the 434-position serine with alanine,
(iii) substitution of the 438-position glutamine with arginine, and
(iv) substitution of the 440-position serine with glutamic acid.
[17] The variant of the above-mentioned [13], wherein the amino acid modifications in the Fc region are
(i) substitution of the 252-position serine with tyrosine,
(ii) substitution of the 254-position serine with threonine, and
(iii) substitution of the 256-position threonine with glutamic acid.
[18] The variant of the above-mentioned [13], wherein the amino acid modifications in the Fc region are (i) substitution of the 308-position isoleucine with proline, and
(ii) substitution of the 434-position serine with tyrosine.

[19] The variant of the above-mentioned [13], wherein the amino acid modifications in the Fc region are
(i) substitution of the 259-position valine with isoleucine,
(ii) substitution of the 308-position isoleucine with phenylalanine, and
(iii) substitution of the 428-position serine with leucine.

[20] The variant of the above-mentioned [13], wherein the amino acid modifications in the Fc region are
(i) substitution of the 252-position serine with threonine,
(ii) substitution of the 254-position serine with threonine,
(iii) substitution of the 256-position threonine with glutamic acid,
(iv) substitution of the 433-position histidine with leucine, and
(v) substitution of the 434-position serine with phenylalanine.

[21] An antibody or Fc fusion protein comprising the variant of any of the above-mentioned [1] to.

Advantageous Effects of Invention

The Fc region variant of the present invention shows an enhanced FcRn binding activity under acidic conditions. Using the variant, therefore, an antibody (IgG) and Fc fusion protein having longer retention in plasma can be provided.

DESCRIPTION OF EMBODIMENTS

The present invention provides a variant of a parent polypeptide containing an Fc region of a dog or cat IgG, that shows a higher binding activity to a dog or cat FcRn (hereinafter to be also referred to as FcRn binding activity) than the FcRn binding activity of the parent polypeptide under acidic conditions, wherein the Fc region contains at least one amino acid modification. It is described in detail in the following.

"FcRn" is structurally similar to a major histocompatibility complex (MHC) class I polypeptide and has 22 to 29% sequence identity with class I MHC molecule in human (reference document for human: Ghetie et al., Immunol. Today (1997) 18 (12), 592-598).

FcRn is expressed as a heterodimer consisting of a soluble β-chain (or light chain) β2-microglobulin (sometimes indicated as β2m) and a transmembrane x-chain (or heavy chain, sometimes indicated as FCGRT). The α chain of FcRn consists of three extracellular domains (α1, α2, α3), and the α1 and α2 domains interact with the FcRn binding domain in the Fc region of antibody (Raghavan et al., Immunity (1994) 1, 303-315).

FcRn forms a complex with in vivo β2-microglobulin. A complex of soluble FcRn with β2-microglobulin is prepared using a conventional recombinant expression method (see "Preparation of FcRn Expression Vector" and "Expression and Purification of FcRn Protein" in Example), and the complex can be used for evaluation of the FcRn binding activity in the present invention. In the present invention, unless otherwise specified, FcRn is used as a complex with (2-microglobulin.

The "parent polypeptide" means a polypeptide before introduction of the amino acid modification of the present invention as opposed to the polypeptide after introduction of the modification. Examples of the parent polypeptide containing the Fc region of dog or cat IgG include a polypeptide containing the Fc region of natural IgG of dog or cat, and preferred is an antibody, particularly a polypeptide constituting the natural IgG of dog or cat. A polypeptide having an Fc region in which an amino acid modification is introduced into the Fc region of the parent polypeptide is also referred to as an Fc region variant, and an IgG composed of the variant is also referred to as a mutant IgG.

The wild-type IgG of dog or cat means a polypeptide that contains the same amino acid sequence as naturally-occurring IgG of dog or cat and belongs to the class of antibody substantially encoded by an immunoglobulin gamma gene.

IgG includes isoforms, and the number thereof varies depending on the animal species. In human, mouse and rat, 4 types of IgG1 to IgG4 are known. There are also four IgG immunoglobulins in dog, and these are defined as caIgG-A, caIgG-B, caIgG-C and caIgG-D (Tang et al., Vet. Immunol. Immunopathol. 80 (3-4), 259-270, 2001). In cat, there are three types of IgG immunoglobulins, the presence of which as IgG1a, IgG1b, and IgG2 has been reported.
1) Kanai, T. H., et al., 2000. Identification of two allelic IgG1 C(H) coding regions (Cgamma1) of cat. Vet. Immunol. Immunopathol. 73 (1), 53-62.
2) Strietzel, C. J., et al., 2014. In Vitro functional characterization of feline IgGs, Vet. Immunol. Immunopathol. 158 (3-4), 214-233.

Examples of the amino acid modification in the Fc region include substitution, insertion, deletion, and the like of amino acids, preferably substitution of amino acids. The number of amino acids to be modified is not particularly limited, and only one amino acid may be modified, or two or more amino acids may be modified. Amino acids at two to several positions, more preferably 2 to 5 positions, are preferably modified. The modification of the amino acid is not particularly limited as long as the EnRn binding activity under acidic pH conditions becomes stronger than that before the modification. The following modifications are preferable.

(In the Case of Dog)
(i) substitution of the 252-position leucine with tyrosine or threonine (L252Y or L252T),
(ii) substitution of the 254-position alanine with threonine (A254T),
(iii) substitution of the 256-position threonine with glutamic acid (T256E),
(iv) substitution of the 308-position isoleucine with proline (I308P),
(v) substitution of the 428-position methionine with leucine (M428L),
(vi) substitution of the 433-position histidine with leucine (H433L),
(vii) substitution of the 434-position asparagine with alanine, serine, tyrosine or phenylalanine (N434A, N434S, N434Y or N434F),
(viii) substitution of the 436-position tyrosine with threonine (Y436T),
(ix) substitution of the 438-position glutamine with arginine (Q438R), and
(x) substitution of the 440-position serine with glutamic acid (S440E)

At least one, preferably two or more, of the modifications are present.

Preferable examples of the modification include the following DFV-1-DFV-6, DFV-8.
DFV-1; N434A, Y436T, Q438R, S440E
DFV-2; M428L, N434A, Y436T, Q438R, S440E
DFV-3; M428L, N434A, Q438R, S440E
DFV-4; L252Y, A254T, T256E
DFV-5; M428L, N434S DFV-6; I308P, N434Y
DFV-8; L252T, A254T, T256E, H433L, N434F
(In the Case of Cat)
  (i) substitution of the 252-position serine with tyrosine or threonine (S252Y or S252T),
  (ii) substitution of the 254-position serine with threonine (S254T),
  (iii) substitution of the 256-position threonine with glutamic acid (T256E),
  (iv) substitution of the 259-position valine with isoleucine (V259I),
  (v) substitution of the 308-position isoleucine with proline or phenylalanine (I308P or I308F),
  (vi) substitution of the 428-position serine with leucine (S428L),
  (vii) substitution of the 433-position histidine with leucine (H433L),
  (viii) substitution of the 434-position serine with alanine, tyrosine or phenylalanine (S434A, S434Y or S434F),
  (ix) substitution of the 436-position histidine with threonine (H436T),
  (x) substitution of the 438-position glutamine with arginine (Q438R), and
  (xi) substitution of the 440-position serine with glutamic acid (S440E)

At least one, preferably two or more, of the modifications are present.

Preferable examples of the modification include the following CFV-1-CFV-4, CFV-6-CFV-8.
  CFV-1; S434A, H436T, Q438R, S440E
  CFV-2; S428L, S434A, H436T, Q438R, S440E
  CFV-3; S428L, S434A, Q438R, S440E
  CFV-4; S252Y, S254T, T256E
  CFV-6; I308P, S434Y
  CFV-7; V259I, I308F, S428L
  CFV-8; S252T, S254T, T256E, H433L, S434F In the present specification, the alphabet displayed on the left side of the number representing the number of amino acid residues up to the substitution site indicates one-letter notation of the amino acid before substitution, and the alphabet displayed on the right side indicates one-letter notation of the amino acid after substitution. The number of amino acid residues up to the substitution site is shown by the EU numbering system of Kabat in the Fc region of human IgG that has been adapted to the Fc region of dog or cat. The "EU numbering system" or "EU Index" is generally used to refer to residues in the heavy chain constant region of an antibody (e.g., Kabat et al., Sequences of Proteins of Immunological Interest. 5th Ed. Public Health Service, National Institutes of Health, Bethesda, Md. (1991)). The "EU numbering system of Kabat" means residue numbering for human IgG1 EU antibody. Unless otherwise specified in the present specification, references to residue numbers is based on the EU numbering of Kabat that has been adapted to the sequences of dog or cat.

The parent polypeptide containing the Fc region of dog or cat IgG to be used in the present invention may be modified to, for example, enhance ADCC (antibody-dependent-cellular-cytotoxicity) activity and CDC (complement-dependent cytotoxicity) activity, to increase protease resistance, to decrease effector function, to decrease the binding activity to complement, to improve antibody heterogeneity and stability, to accelerate the clearance of antigen, to cause repeated binding to multiple molecule antigens, to reduce the pI of the constant region for the purpose of increasing blood retention property, to have a binding ability to other antigens and the like. For more details, the technique of Fc engineering described in Current Pharmaceutical Biotechnology, 2016, 17, 1298-1314 can be referred to. References to residue numbers in this literature are based on the EU numbering system of Kabat. The type of these modifications may be, for example, any of substitution, deletion, addition, insertion, and modification of amino acids, or combinations thereof, and preferred is substitution of amino acids.

The three-letter notation and the one-letter notation of amino acids used in this specification correspond as follows.
  alanine: Ala: A
  arginine: Arg: R
  asparagine: Asn: N
  aspartic acid: Asp: D
  cysteine: Cys: C
  glutamine: Gln: Q
  glutamic acid: Glu: E
  glycine: Gly: G
  histidine: His: H
  isoleucine: Ile: I
  leucine: Leu: L
  lysine: Lys: K
  methionine: Met: M
  phenylalanine: Phe: F
  proline: Pro: P
  serine: Ser: S
  threonine: Thr: T
  tryptophan: Trp: W
  tyrosine: Tyr: Y
  valine: Val: V Such modifications (deletion, substitution, insertion, addition) of amino acid can be introduced into an amino acid sequence by partially modifying the base sequence encoding the amino acid sequence. For this partial modification of the base sequence, known methods such as known site-specific mutagenesis method (Site specific mutagenesis) (Proc Natl Acad Sci USA., 1984 Vol. 81 5662-5666; Sambrook et al., Molecular Cloning A Laboratory Manual (1989) Second edition, Cold Spring Harbor Laboratory Press), Overlap extension PCR and the like can be appropriately adopted. In addition, a plurality of known methods may be adopted as a method for modifying into an amino acid other than the natural amino acid (Annu. Rev. Biophys. Biomol. Struct. (2006) 35, 225-249, Proc. Natl. Acad. Sci. U.S.A. (2003) 100 (11), 6353-6357). For example, a cell-free translation system in which a complementary amber suppressor tRNA of a UAG codon (amber codon), which is one of the stop codons, contains a tRNA to which an unnatural amino acid is bound (Clover Direct (Protein Express)) and the like are preferably used.

Also, the methods for modifying the Fc region of human IgG1 carried out in the following literatures can be referred to.
  Drug Metab Dispos. 2007 January; 35 (1): 86-94,
  Int Immunol. 2006 December; 18 (12): 1759-69,
  J Biol Chem. 2001 Mar. 2; 276 (9): 6591-604,
  J Biol Chem. 2007; 282 (3): 1709-17,
  J Immunol. 2002; 169 (9): 5171-80,
  J Immunol. 2009; 182 (12): 7663-71,
  Molecular Cell, Vol. 7, 867-877, April 2001,
  Nat Biotechnol. 1997 July; 15 (7): 637-40,
  Nat Biotechnol. 2005 October; 23 (10): 1283-8,
  Proc Natl Acad Sci USA. 2006 Dec. 5; 103 (49): 18709-14, EP2154157, US20070141052, WO2000/042072, WO2002/060919, WO2006/020114, WO2006/031370, WO2010/033279, WO2006/053301, WO2009/086320.

In the present invention, "having activity" means that, in a system capable of measuring the activity, the measured value becomes higher than the background value (or value when negative control was measured) in the system. For example, having a binding activity means that, in a system capable of measuring the binding activity, such as ELISA, FACS, Biacore and the like, the measured value becomes higher than the background value. In the present invention, the measured value is preferably not less than 2 times, more preferably not less than 3 times, further preferably not less than 5 times, particularly preferably not less than 10 times, higher than the background value.

For example, in the present invention, the reciprocal of KD (dissociation constant) can be used as the value of FcRn binding activity. The KD value of the Fc region variant provided by the present invention can be measured by using, for example, a known method of Biacore (GE Healthcare). In the case of Biacore, specifically, the Fc region variant provided by the present invention or an antibody molecule containing the variant is immobilized on a sensor chip, and the KD value can be measured by flowing FcRn as an analyte therein. By performing the measurement in the Fc region of wild-type IgG (wild-type Fc) and the Fc region of mutant IgG (Fc region variant), and under acidic pH conditions and neutral pH conditions, the values of KD (Fc region variant)/KD (wild-type Fc) and KD (pH acidic)/KD (PH neutral) can be calculated.

It is also possible to use kd (Dissociation rate constant) instead of KD.

In the present specification, higher binding activity to dog or cat FcRn than to the parent polypeptide means that, for example, the activity of binding to dog or cat FcRn is not less than 105%, preferably not less than 110%, not less than 115%, not less than 120%, not less than 125%, particularly preferably not less than 130%, not less than 135%, not less than 140%, not less than 145%, not less than 150%, not less than 155%, not less than 160%, not less than 165%, not less than 170%, not less than 175%, not less than 180%, not less than 185%, not less than 190%, not less than 195%, not less than 2 times, not less than 2.5 times, not less than 3 times, not less than 3.5 times, not less than 4 times, not less than 4.5 times, not less than 5 times, not less than 7.5 times, not less than 10 times, not less than 20 times, not less than 30 times, not less than times, not less than 50 times, not less than 60 times, not less than 70 times, not less than 80 times, not less than 90 times, not less than 100 times, that of the parent polypeptide.

If properties that render the binding activity to dog or cat FcRn stronger than that of natural dog or cat IgG under acidic pH conditions can be imparted to the Fc region variant of the present invention, and if IgG can be constituted using the Fc region variant, the efficiency of recycling from within endosome to within plasma increases since the binding of IgG to FcRn under acidic conditions increases, and as a result, retention in plasma can be improved or enhanced.

In the present invention, the binding activity to dog or cat FcRn under acidic conditions means FcRn binding activity at pH 4.0-pH 6.5. It preferably means FcRn binding activity at pH 5.0-pH 6.5, further preferably dog or cat FcRn binding activity at any of pH 5.5, 5.6, 5.7, 5.8, 5.9, 6.0, 6.1, 6.2, 6.3, 6.4, 6.5, particularly preferably, FcRn binding activity in early endosome of living organism approximately at pH 5.8-pH 6.0. In the present invention, the binding activity to dog or cat FcRn under neutral conditions means FcRn binding activity at pH 6.7-pH 10.0. Preferably, it means FcRn binding activity at pH 7.0-pH 9.0, further preferably FcRn binding activity at any of pH 7.0, 7.1, 7.2, 7.3, 7.4, 7.5, 7.6, 7.7, 7.8, 7.9, 8.0, particularly preferably FcRn binding activity in plasma of living organism approximately at pH 7.4.

When it is difficult to measure the binding affinity with FcRn accurately because the affinity is very low at pH 7.4, pH 7.0 can be used instead of pH 7.4. As the temperature used for the measurement conditions, the binding affinity with FcRn may be measured at any temperature of 10° C.-50° C. Preferably, to determine the binding affinity for FcRn, any temperature of 15° C.-40° C. is used. Although not particularly limited, 25° C. is one of the preferred embodiments.

In the present invention, a polynucleotide encoding the Fc region variant of the present invention can be provided. Polynucleotide is mainly constituted of DNA, RNA, other nucleic acid analog, and the like. The polynucleotide encoding the Fc region variant of the present invention is bound to a polynucleotide encoding other region constituting the antibody to construct a gene encoding the antibody, and the gene is inserted into a suitable expression vector (where necessary, two kinds of expression vectors may also be used). Alternatively, a polynucleotide encoding the Fc region variant of the present invention is bound to a polynucleotide encoding a protein such as cytokine, soluble membrane receptor and the like to construct a gene encoding the Fc fusion protein, and the gene is inserted into a suitable expression vector. At that time, the gene is incorporated into an expression vector such that it is expressed in an expression control region, for example, under the control of an enhancer or a promoter. Then, a host cell is transformed with the expression vector and the antibody is expressed. At that time, a suitable combination of a host and an expression vector can be used.

The type of vector that can be used is not particularly limited as long as it stably retains the inserted gene, and various commercially available vectors can be used. Examples of the vector for gene cloning include M13-based vectors, pUC-based vectors, and the like. When a vector is used for the purpose of producing the Fc region variant provided by the present invention, an expression vector is particularly useful. The expression vector is not particularly limited as long as it expresses polypeptide in vitro, in *Escherichia coli*, in cultured cells, or in an individual organism. Examples of the vector include pBEST vector (manufactured by Promega) and the like as vector for expression in vitro, pGEX, pET, pBluescript® vector, a high-copy-number pUC based plasmid with ampicillin resistance, (manufactured by Stratagene) and the like as vector for expression in *Escherichia coli*, pME18S-FL3 vector (GenBank Accession No. AB009864) and the like as vector for expression in cultured cells, pcDNA as vector for expression in animal cells, pME18S vector (Mol Cell Biol. 8:466-472 (1988)) for expression in individual organisms, and the like. The polynucleotide of the present invention can be inserted into a vector by using, for example, In-Fusion Advantage PCR Cloning Kit (manufactured by Clontech).

The host cell that can be used is not particularly limited and, for example, *Escherichia coli*, various animal cells, and the like can be preferably used. The host cell can be used, for example, as a production system for producing or expressing the Fc region variant of the present invention and an antibody or Fc fusion protein containing the Fc region variant. The production system includes in vitro and in vivo production systems. Examples of the in vitro production system include a production system using eukaryotic cells and a production system using prokaryotic cells.

Eukaryotic cell that can be used as a host cell includes, for example, animal cell, plant cell, and fungal cell. Animal cell includes mammalian cells such as CHO (J. Exp. Med. (1995) 108:94.0), COS, HEK293, 3T3, myeloma, BHK (baby hamster kidney), HeLa, Vero, etc., amphibia cells such as *Xenopus* oocyte (Valle et al., Nature (1981) 291:338-340), and insect cells such as Sf9, Sf21, Tn5. Preferably, CHO-DG44, CHO-DX11B, COS7, HEK293, and BHK are used. When a large amount of expression is desired, CHO is particularly preferable. For introduction of a vector into a host cell, for example, a method known to those of ordinary skill in the art such as calcium phosphate method, DEAE dextran method, a method using cationic ribosome DOTAP (manufactured by Boehringer Mannheim), electroporation method, lipofection method, microinjection method and the like can be used. In addition, Free Style 293 Expression System (manufactured by Invitrogen) can also be used to perform steps from gene transfer to polypeptide expression.

The obtained Fc region variant or an antibody or Fc fusion protein containing the Fc region variant can be isolated intracellularly or extracellularly (medium, milk, and the like) and purified as substantially pure and homogeneous molecules. Separation and purification of the Fc region variant or the antibody or Fc fusion protein containing the Fc region variant may be performed using the separation and purification method generally used in the purification of polypeptides, and is not limited in any way. For example, column chromatography, filtration, ultrafiltration, salting out, solvent precipitation, solvent extraction, distillation, immunoprecipitation, SDS-polyacrylamide gel electrophoresis, isoelectric focusing, dialysis, recrystallization and the like can be appropriately selected and combined to perform separation and purification.

Where necessary, the Fc region variant of the present invention or an antibody or Fc fusion protein containing the Fc region variant can also be arbitrarily modified or peptide can be partially removed therefrom by reaction with an appropriate protein modifying enzyme. As the protein modifying enzyme, trypsin, chymotrypsin, lysyl endopeptidase, protein kinase, glucosidase and the like are used.

The antibody or Fc fusion protein containing the Fc region variant of the present invention shows enhanced FcRn binding activity under acidic conditions, and long retention in plasma. Accordingly, the present invention provides a pharmaceutical composition containing the antibody as the active ingredient and targeting dog or cat. While pharmaceutical compositions can be used for treating diseases, the pharmaceutical composition provided by the present invention can be used to treat diseases in which one of the causes is considered to be the antigen of the antibody. In the present specification, "treatment" means to obtain pharmacological and/or physiological effects. The effect can be prophylactic in that it completely or partially prevents the symptoms of the disease, and can also be therapeutic in that it completely or partially treats the symptoms of the disease. The "treatment" in the present specification includes all treatments for diseases in dogs or cats, or animal species closely related thereto.

The pharmaceutical composition provided by the present invention can be formulated by a method known to those skilled in the art (e.g., Remington's Pharmaceutical Science, latest edition, Mark Publishing Company, Easton, USA). Generally, it contains pharmaceutically acceptable additives that are conventionally used in the art and suitable for administration to a subject for therapeutic, diagnostic or prophylactic purposes. For example, when formulated as a solid, for example, a filler such as lactose and the like, a binder such as carboxymethyl cellulose, gelatin and the like, a coloring agent, a coating agent and the like can be used, and such agent is suitable for oral administration. In addition, for example, white petrolatum, a cellulose derivative, a surfactant, polyethylene glycol, silicone, olive oil, and the like may be added as a carrier or an excipient and applied to the affected part as an external medicine in the form of cream, milky lotion, lotion or the like. When formulated as a liquid, it can contain generally-used physiologically acceptable solvent, emulsifier, and stabilizer. Examples of the solvent include water, PBS, isotonic physiological saline and the like; examples of the emulsifier include polyoxyethylene-based surfactant, fatty acid-based surfactant, silicone, and the like; and examples of the stabilizer include dog serum albumin, polyols such as gelatin and the like, saccharides such as sorbitol, trehalose and the like, and the like. Composition for oral administration can form solution, suspension, tablet, pill, capsule, sustained release formulation, mouthwash or powder.

While the method for administering the pharmaceutical composition of the present invention is not particularly limited, therapeutic effects can be expected most by injection administration. The injection administration method is not limited to any of intravenous administration, intramuscular administration, subcutaneous administration, intraperitoneal administration, and intrathoracic administration.

The dose will be determined depending on the type of antibody used (type of antigen), size of individual, administration method, type of disease, symptoms, and the like. It only needs to be administered in an amount sufficient to show a therapeutic effect and a prophylactic effect.

All prior art documents cited in the present specification are incorporated in the present specification for reference.

EXAMPLE

The present invention is now explained further in the following by referring to Examples, which are not to be construed as limitative.

Example 1. Preparation of IgG Expression Vector Having Wild-Type Fc

Gene synthesis of the Fc region of wild-type dog IgG H chain registered in GenBank: AF354265.1 (SEQ ID NO: 1, hereinafter dog wild type Fc, abbreviated as dog wtFc) and the Fc region of wild-type cat IgG H chain registered in GenBank: AB016710.1 (SEQ ID NO: 2, hereinafter cat wild type Fc, abbreviated as cat wtFc) was performed by GenScript Japan Inc. based on the amino acid sequence.

Gene synthesis of the region from Fd to the hinge of the IgG H chain (SEQ ID NO: 3, hereinafter Fd-Hinge) and the entire region of the IgG L chain (SEQ ID NO: 4, hereinafter L chain) was performed by GenScript Japan Inc. based on the amino acid sequence of a humanized anti-human IgE antibody omalizumab registered in IMGT (reference imgt.org) under IMGT/mAb-DB ID: 77, such that an amino acid consisting of MEFGLSWVELVALFRGVQC (SEQ ID NO: 5) is attached as a secretory signal peptide to the N-terminal side of the Fd-Hinge and an amino acid consisting of MDMRVPAQLLGLLLLWLSGARC (SEQ ID NO: 6) is attached to the N-terminal side of the L chain.

The synthesized Fd-Hinge gene of omalizumab containing the secretory signal peptide was amplified by the PCR method, connected using the In-Fusion HD Cloning Kit (manufactured by Clontech) (hereinafter In-Fusion Kit) to each of dog wtFc gene and cat wtFc gene similarly amplified by the PCR method such that Fd-Hinge was on the N-terminal side and wtFc on the C-terminal side, simultaneously inserted directly under the CMV promoter of pcDNA3.1 (+) (Invitrogen), *Escherichia coli* DH5α was transformed, and the plasmid was extracted to give H chain expression vectors pcDNA3. 1 (+)/omalizumab Fd-dog wtFc and pcDNA3. 1 (+)/omalizumab Fd-cat wtFc.

The synthesized L chain gene of omalizumab containing the secretory signal peptide was amplified by the PCR method, inserted directly under the CMV promoter of pcDNA3. 1 (+) (Invitrogen) using the In-Fusion kit, *Escherichia coli* DH5α was transformed, and the plasmid was extracted to give L chain expression vector pcDNA3.1 (+)/omalizumab Lch.

In all cases, when using the In-Fusion kit, *Escherichia coli* DH5α competent cells (TOYOBO) were transformed with the DNA solution after the In-Fusion reaction, according to the method described in the attached manual. The obtained transformant was cultured overnight at 37° C. in LB liquid medium containing 100 μg/mL ampicillin, and a plasmid was extracted therefrom using the NucleoBond Xtra Midi Kit (Takara Bio Inc.). The base sequence of the obtained expression vector was determined by a method known to those skilled in the art, and it was confirmed that the protein of the amino acid sequence of interest was encoded.

```
amino acid sequence of omalizumab Fd-Hinge region
                                             (SEQ ID NO: 3)
EVQLVESGGGLVQPGGSLRLSCAVSGYSITSGYSWNWIRQAPGKGLEWVA

SITYDGSTNYNPSVKGRITISRDDSKNTFYLQMNSLRAEDTAVYYCARGS

HYFGHWHFAVWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCP amino acid sequence of wild-type dog IgG H chain
Fc region
                                             (SEQ ID NO: 1)
APEMLGGPSVFIFPPKPKDTLLIARTPEVTCVVVDLDPEDPEVQISWFVD

GKQMQTAKTQPREEQFNGTYRVVSVLPIGHQDWLKGKQFTCKVNNKALPS

PIERTISKARGQAHQPSVYVLPPSREELSKNTVSLTCLIKDFFPPDIDVE

WQSNGQQEPESKYRTTPPQLDEDGSYFLYSKLSVDKSRWQRGDTFICAVM

HEALHNHYTQESLSHSPGK amino acid sequence of wild-type cat IgG H chain
Fc region
                                             (SEQ ID NO: 2)
PPEMLGGPSIFIFPPKPKDTLSISRTPEVTCLVVDLGPDDSDVQITWFVD

NTQVYTAKTSPREEQFNSTYRVVSVLPILHQDWLKGKEFKCKVNSKSLPS

PIERTISKAKGQPHEPQVYVLPPAQEELSRNKVSVTCLIKSFHPPDIAVE

WEITGQPEPENNYRTTPPQLDSDGTYFVYSKLSVDRSHWQRGNTYTCSVS

HEALHSHHTQKSLTQSPGK amino acid sequence of omalizumab L chain
                                             (SEQ ID NO: 4)
DIQLTQSPSSLSASVGDRVTITCRASQSVDYDGDSYMNWYQQKPGKAPKL

LIYAASYLESGVPSRFSGSGSGTDFTLTISSLQPEDFATYYCQQSHEDPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC
```

Example 2. Preparation of IgG H Chain Expression Vector Having Modified Fc

Primers encoding mutant amino acids were designed so that the amino acid sequence of the Fc region would be substituted by the amino acid shown in the following Table 1 "Position of dog, cat Fc modification". Using H chain expression vectors pcDNA3.1 (+)/omalizumab Fd-dog wtFc and pcDNA3.1 (+)/omalizumab Fd-cat wtFc prepared in Example 1 as templates, a DNA fragment in which a mutation was introduced into the Fc region was amplified by the PCR method using the designed primers, and an H-chain expression vector in which a mutation was introduced only into arbitrary sites of the Fc serving as the template was prepared by ligating the amplified DNA fragments by using the In-Fusion kit.

In all cases, when using the In-Fusion kit, *Escherichia coli* DH5α competent cells (TOYOBO) were transformed with the DNA solution after the In-Fusion reaction, according to the method described in the attached manual. The obtained transformant was cultured overnight at 37° C. in LB liquid medium containing 100 μg/mL ampicillin, and a plasmid was extracted therefrom using the NucleoBond Xtra Midi Kit (Takara Bio Inc.). The base sequence of the obtained expression vector was determined by a method known to those skilled in the art, and it was confirmed that the protein of the amino acid sequence of interest was encoded.

Various Fc region variants were prepared by introducing the amino acid substitutions shown in the following Table 1 "Position of dog, cat Fc modification" into the Fc regions of dog-wtFc and cat-wtFc.

TABLE 1

| | | | |
|---|---|---|---|
| Position of dog, cat Fc modification | | | |
| | name of variant | modification (when human EU numbering is adapted to dog sequences) | modification (amino acid at the start of dog Fc region_SEQ ID NO: 1 as 1) |
| dog | DFV-1 | N434A/Y436T/Q438R/S440E | N206A/Y208T/Q210R/S212E |
| | DFV-2 | M428L/N434A/Y436T/Q438R/S440E | M200L/N206A/Y208T/Q210R/S212E |
| | DFV-3 | M428L/N434A/Q438R/S440E/ | M200L/N206A/Q210R/S212E/ |
| | DFV-4 | L252Y/A254T/T256E | L22Y/A24T/T26E |
| | DFV-5 | M428L/N434S | M200L/N206S |
| | DFV-6 | I308P/N434Y | I78P/N206Y |
| | DFV-7 | V259I/I308F/M428L | V29I/I78F/M200L |
| | DFV-8 | L252Y/A254T/T256E/H433L/N434F | L22Y/A24T/T26E/H205L/N206F |
| | name of variant | modification (when human EU numbering is adapted to cat sequences) | modification (amino acid at the start of cat Fc region_SEQ ID NO: 2 as 1) |
| cat | CFV-1 | S434A/H436T/Q438R/S440E | S206A/H208T/Q210R/S212E |
| | CFV-2 | S428L/S434A/H436T/Q438R/S440E | S200L/S206A/H208T/Q210R/S212E |
| | CFV-3 | S428L/S434A/Q438R/S440E | S200L/S206A/Q210R/S212E |
| | CFV-4 | S252Y/S254T/T256E | S22Y/S24T/T26E |
| | CFV-5 | I308P/S434Y | I78P/S206Y |
| | CFV-6 | V259I/I308F/S428L | V29I/I78F/S200L |
| | CFV-7 | S252Y/S254T/T256E/H433L/S434F | S22Y/S24T/T26E/H205L/S206F |
| | CFV-8 | | |

Example 3. Antibody Expression and Purification

The expression vectors obtained in Example 1 and Example 2 were transiently introduced into FreeStyle 293 cells (Invitrogen) to express the antibody. After collecting the obtained culture supernatant, the culture supernatant was obtained by passing through a 0.22 μm filter Millex (R)-GP (Merck Millipore). The obtained culture supernatant was eluted with 50 mM acetic acid by affinity chromatography using MabSelect SuRe® chromatography resin (GE Healthcare), and the antibody was purified by a neutralization treatment by the addition of 1.5M Tris-HCl, pH 7.5. The obtained antibody was subjected to buffer substitution with a buffer of 20 mM Histidine-HCl, 150 mM NaCl, pH 6.5, using an ultrafiltration membrane (Merck Millipore) capable of fractionating 30 kDa. For the purified antibody concentration, the absorption at 280 nm was measured using a spectrophotometer, and the antibody concentration was calculated from the obtained value and using the absorption coefficient calculated by the method of PACE et al. (Protein Science (1995); 4, 2411-2423).

Example 4. Preparation of FcRn Expression Vector

Gene synthesis of an extracellular region of dog FCGRT registered in GenBank: XP_005616366.1 (SEQ ID NO: 7, hereinafter abbreviated as dog FCGRT) and extracellular region of cat FCGRT registered in GenBank: XP_023100998.1 (SEQ ID NO: 8, hereinafter abbreviated as cat FCGRT) to afford each amino acid sequence with Histag (HHHHHHHH) (SEQ ID NO: 9) attached to the C-terminal side, and cloning of the synthesized genes into pcDNA3. 1 (+) (Invitrogen) and the plasmid extraction were performed by GenScript Japan Inc. The obtained expression vectors were pcDNA3.1 (+)/dog FCGRT, pcDNA3.1 (+)/cat FCGRT.

Gene synthesis of dogβ2m registered in GenBank: NP_001271408 (SEQ ID NO: 10, hereinafter abbreviated as dog β2m) and catβ2m registered in GenBank: NP_001009876 (SEQ ID NO: 11, hereinafter abbreviated as cat 2m) based on the amino acid sequence, and cloning of the synthesized genes into pcDNA3.1 (+) (Invitrogen) and the plasmid extraction were performed by GenScript Japan Inc. The obtained expression vectors were pcDNA3. 1 (+)/dogβ2m, pcDNA3. 1 (+)/catβ2m.

```
amino acid sequence of dog FCGRT extracellular
region
                                   (SEQ ID NO: 7)
MGVPRPRSWGLGFLLFLLPTLRAADSHLSLLYHLTAVSAPPPGTPAFWA

SGWLGPQQYLSYNNLRAQAEPYGAWVWENQVSWYWEKETTDLRTKEGLF

LEALKALGDGGPYTLQGLLGCELGPDNTSVPVAKFALNGEDFMTFDPKL

GTWNGDWPETETVSKRWMQQAGAVSKERTFLLYSCPQRLLGHLERGRGN

LEWKEPPSMRLKARPGSPGFSVLTCSAFSFYPPELQLRFLRNGLAAGSG

EGDFGPNGDGSFHAWSSLTVKSGDEHHYRCLVQHAGLPQPLTVELESPA

KSS amino acid sequence of cat FCGRT extracellular
region
                                   (SEQ ID NO: 8)
MGVPRPQPWGLGFLLFLLPTLRAAESHLSLLYHLTAVSSPAPGTPAFWV SGWLGPQQYLSYNNLRAQAEPCGAWVWENQVSWYWEKETTDLRNKQELF
```
```
LEALKVLGEGGPYTLQGLLGCELGPDNASVPVAKFALNGEDFMDFDPKL

GTWSGEWPETETISKRWMQEAGAVSKERTFLLNSCPQRLLGHLERGRGN

LEWKEPPSMRLKARPGSPGFSVLTCSAFSFYPPELQLRFLRNGLAAGSG

EGDFGPNGDGSFHAWSSLTVKSGDEHHYRCLVQHAGLPQPLTVELESPA

KSS amino acid sequence of dog β2m
                                   (SEQ ID NO: 10)
MAPRPALATAGFLALLLILLAACRLDAVQHPPKIQVYSRHPAENGKPNF

LNCYVSGFHPPEIEIDLLKNGKEMKAEQTDLSFSKDWTFYLLVHTEFTP

NEQDEFSCRVKHVTLSEPQIVKWDRDN amino acid sequence of cat β2m
                                   (SEQ ID NO: 11)
MARFVVLVLLGLLYLSHLDAVQHSPKVQVYSRHPAENGKPNFLNCYVSG

FHPPQIDITLMKNGKKMEAEQTDLSFNRDWTFYLLVHTEFTPTVEDEYS

CQVNHTTLSEPKVVKWDRDM
```

Example 5. Expression and Purification of FcRn Protein

The expression vectors in a combination of pcDNA3. 1 (+)/dog FCGRT and pcDNA3. 1 (+)/dogβ2m, and a combination of pcDNA3.1 (+)/cat FCGRT and pcDNA3.1 (+)/catβ2m obtained in Example 4 were co-transfected into FreeStyle 293 cells (Invitrogen) to express dog and cat FcRn proteins. After culturing and collecting the obtained culture supernatant, the culture supernatant was obtained by passing through a 0.22 μm filter Millex (R)-GP (Merck Millipore). The obtained culture supernatant was purified in the following two steps in principle. In the first step, affinity column chromatography on His tags (His Trap HP) was performed and the protein of interest was fractionated by gradient elution of imidazole concentration using buffers of 20 mM Tris, 0.5 M NaCl, 10 mM imidazole, pH 7.4 and 20 mM Tris, 0.5 M NaCl, 500 mM imidazole, pH 7.4. In the second step, substitution with D-PBS (−), pH 7.0 buffer and size fractionation were performed using gel filtration column chromatography (Superdex200) to purify the protein of interest. For the purified protein, the absorption at 280 nm was measured using a spectrophotometer, and the concentration of the purified protein was calculated from the obtained value and using the absorption coefficient calculated by the method of PACE et al. (Protein Science (1995); 4, 2411-2423).

Experimental Example 1: Interaction Measurement by Biacore (Binding Analysis)

Evaluation of Binding Ability of Obtained Antibody to Dog and Cat FcRns

The obtained antibody was evaluated using BiacoreX100 (GE Healthcare) to determine whether it has the binding ability to dog and cat FcRn. As the condition in plasma, pH 7.4 was set. As the condition in endosome, pH 6.0 was set (acidic condition). The antibody of interest was captured by Sensor chip Protein L (GE Healthcare), and dog and cat FcRns were used as antigens. The measurement was performed using three kinds of running buffers (1; 50 mmol/L phosphoric acid, 150 mmol/L NaCl, 0.05% (w/V) Tween-20, pH 7.4, 2; 50 mmol/L phosphoric acid, 150 mmol/L NaCl, 0.05% (w/v) Tween-20, pH 7.0, 3; 50 mmol/L phosphoric acid, 150 mmol/L NaCl, 0.05% (w/v) Tween-20, pH 6.0).

Method for Performing Measurement

The antibody diluted with a running buffer was injected at a flow rate of 5 μL/min for 1 min to allow for capture by a sensor chip. Then, FcRn diluted to 1600, 800, 400, 200, 100 nM with the running buffer and the running buffer (as a reference solution) were injected at a flow rate of 30 μL/min for 2 min to cause interaction with the captured antibody. Furthermore, the running buffer was flown for 10 min at a flow rate of 30 μL/min to observe dissociation of FcRn. Finally, 10 mmol/L Glycine-HCl, pH 1.7 was injected twice at a flow rate of 30 μL/min for 1 min to regenerate the sensor chip. The antibody captured on the sensor chip was washed by the regeneration operation, and the sensor chip was used repeatedly.

Since the binding affinity between wild-type IgG and FcRn is very low at pH 7.4, calculation of the KD value is difficult. Therefore, when accurate measurement of the affinity is difficult, the measurement was performed using pH 7.0 instead of pH 7.4.

Analysis Method

To calculate the dissociation constant KD (mol/L) to FcRn of the antibody containing each Fc region variant, kinetic analysis was performed according to the following method. First, the desired antibody was captured using the above-mentioned sensor chip, allowed to interact with FcRn diluted with running buffer. The measurement results were globally fitted to the obtained sensorgram by Biacore Evaluation Software in a 1:1 binding model to calculate the binding rate constant ka (L/mol/s) and the dissociation rate constant kd (1/s), and the dissociation constant KD (mol/L) was calculated from the values.

When the obtained sensorgram is box-shaped and reaches an equilibrium state immediately, the equilibrium value (=binding amount) during FcRn injection reflects the dissociation constant KD (M). The dissociation constant KD (mol/L) of each variant to FcRn was calculated by performing steady state affinity analysis using Biacore Evaluation Software on the sensorgram obtained as the measurement result of Biacore.

The behavior of molecules interacting in the 1:1 binding model on Biacore can be expressed by the formula 1 below.

$$Req = C \times Rmax/(KD+C) + RI \quad \text{(formula 1)}$$

Each item in the above-mentioned formula means as follows.

Req (RU): steady state binding levels
Rmax (RU): affinity binding capacity of the surface of analyte
RI (RU): bulk refractive index contribution in the sample
C (M): analyte concentration
KD (M): equilibrium dissociation constant The results are shown in the following Tables.

TABLE 2

Comparison of KD (mol/L) values of dog Fc region variant and dog FcRn

| name of variant | KD (mol/L) under measurement pH condition | | | | KD (variant)/ KD (wild-type) at pH 6.0 | KD (pH6.0)/ KD (pH7.4) | KD (pH6.0)/ KD (pH7.0) |
|---|---|---|---|---|---|---|---|
| | pH7.4 | pH7.0 | pH6.0 | | | | |
| Wild-type Fc | | 2.37E−06 | 1.99E−06 | 1.77E−06 | 2.01E−06 | 1.00 | | 0.840 |
| DFV-1 | | 5.43E−07 | | | 0.27 | | |
| DFV-2 | 3.43E−06 | 3.87E−07 | | | 0.19 | | 0.113 |
| DFV-3 | | 3.71E−07 | | | 0.19 | | |
| DFV-4 | 1.81E−05 | 1.09E−07 | | | 0.05 | | 0.006 |
| DFV-5 | 2.30E−06 | | 8.20E−07 | | 0.46 | | 0.357 |
| DFV-6 | | 2.64E−07 | | 2.63E−08 | 0.01 | | 0.100 |
| DFV-7 | | | | 2.03E−06 | 1.01 | | |
| DFV-8 | 6.85E−06 | | | 6.96E−08 | 0.03 | | 0.010 |

TABLE 3

Comparison of KD (mol/L) values of cat Fc region variant and cat FcRn

| name of variant | KD (mol/L) under measurement pH condition | | | KD (variant)/ KD (wild-type) at pH 6.0 | KD (pH6.0)/ KD (pH7.4) | KD (pH6.0)/ KD (pH7.0) |
|---|---|---|---|---|---|---|
| | pH7.4 | pH7.0 | pH6.0 | | | |
| Wild-type Fc | | 7.58E−06 | 6.32E−07 | 7.00E−07 | 1.00 | | 0.083 |
| CFV-1 | | 4.04E−07 | | 0.64 | | |
| CFV-2 | 1.41E−05 | 6.48E−08 | | 0.10 | | 0.005 |
| CFV-3 | | 4.62E−08 | | 0.07 | | |
| CFV-4 | 4.61E−06 | 2.14E−08 | | 0.03 | | 0.005 |
| CFV-6 | 1.06E−06 | | 2.70E−09 | 0.00 | | 0.003 |
| CFV-7 | | | 5.10E−08 | 0.07 | | |
| CFV-8 | 6.39E−06 | | 3.93E−08 | 0.06 | | 0.006 |

TABLE 4

Comparison of KD (mol/L) values of dog Fc region variant and dog FcRn at pH 6.0

| name of variant | KD (mol/L) under pH 6.0 condition | | | activity of Fc region variant with FcRn binding activity of wild-type Fc as 1 |
|---|---|---|---|---|
| wild-type Fc | 1.99E−06 | 1.77E−06 | 2.01E−06 | 1.0 |
| DFV-1 | 5.43E−07 | | | 3.7 |
| DFV-2 | 3.87E−07 | | | 5.1 |
| DFV-3 | 3.71E−07 | | | 5.4 |
| DFV-4 | 1.09E−07 | | | 18.2 |
| DFV-5 | | 8.20E−07 | | 2.2 |
| DFV-6 | | | 2.63E−08 | 76.3 |
| DFV-7 | | | 2.03E−06 | 1.0 |
| DFV-8 | | | 6.96E−08 | 28.8 |

TABLE 5

Comparison of KD (mol/L) values of cat Fc region variant and cat FcRn at pH 6.0

| name of variant | KD (mol/L) under pH 6.0 condition | | activity of Fc region variant with FcRn binding activity of wild-type Fc as 1 |
|---|---|---|---|
| wild-type Fc | 6.32E−07 | 7.00E−07 | 1.0 |
| CFV-1 | 4.04E−07 | | 1.6 |
| CFV-2 | 6.48E−08 | | 9.8 |
| CFV-3 | 4.62E−08 | | 13.7 |
| CFV-4 | 2.14E−08 | | 29.5 |
| CFV-6 | | 2.70E−09 | 259.3 |
| CFV-7 | | 5.10E−08 | 13.7 |
| CFV-8 | | 3.93E−08 | 17.8 |

These results obtained are not always consistent with the results reported in human. In particular, the amino acid substitution of DFV-7 significantly enhanced the binding to FcRn under acidic conditions in human (Zelevsky, J et al, Nat Technol (2010) 28, 157-159), whereas such effect was not found at all in dogs. This strongly indicates the importance of confirming effects by using FcRn of dog and cat in the preparation of an antibody drug for dogs and cats.

INDUSTRIAL APPLICABILITY

The Fc region variant of the present invention shows an enhanced FcRn binding activity under acidic conditions. Using the variant, therefore, an antibody (IgG) and Fc fusion protein having longer retention in plasma can be provided.

This application is based on a patent application No. 2018-228448 filed in Japan (filing date: Dec. 5, 2018), the contents of which are incorporated in full herein.

The invention claimed is:

1. A variant of a parent polypeptide comprising an Fc region of a cat IgG, that shows a higher binding activity to a cat neonatal Fc receptor (FcRn) than a binding activity of the parent polypeptide to a cat FcRn under acidic conditions, wherein the Fc region comprises at least the following amino acid modification:

(i) substitution of the 428-position serine with leucine,
(ii) substitution of the 434-position serine with alanine,
(iii) substitution of the 438-position glutamine with arginine, and
(iv) substitution of the 440-position serine with glutamic acid, wherein the numbering of amino acid position in the Fc region is based on EU Index of Kabat using Fc region of human antibody as the standard.

2. An antibody or Fc fusion protein comprising the variant according to claim 1.

* * * * *

UNITED STATES PATENT AND TRADEMARK OFFICE
CERTIFICATE OF CORRECTION

PATENT NO. : 12,351,622 B2  
APPLICATION NO. : 17/311085  
DATED : July 8, 2025  
INVENTOR(S) : Ryota Nakao et al.

Page 1 of 1

It is certified that error appears in the above-identified patent and that said Letters Patent is hereby corrected as shown below:

In the Claims

At Column 31, Line 16, "at least the" should be -- the --.

Signed and Sealed this  
Tenth Day of February, 2026

John A. Squires  
*Director of the United States Patent and Trademark Office*